US005385911A

United States Patent [19]

Sunkara et al.

[11] Patent Number: 5,385,911

[45] Date of Patent: Jan. 31, 1995

[54] ANTI-HERPES CASTANOSPERMINE ESTERS

[75] Inventors: Sai P. Sunkara, Cincinnati, Ohio; Paul S. Liu, Chevy Chase, Md.; A. Stanley Tyms; Debra L. Taylor, both of London, United Kingdom

[73] Assignee: Merrell Dow Pharmaceuticals Inc., Cincinnati, Ohio

[21] Appl. No.: 41,532

[22] Filed: Apr. 1, 1993

Related U.S. Application Data

[63] Continuation of Ser. No. 808,150, Dec. 16, 1991, abandoned.

[30] Foreign Application Priority Data

Dec. 18, 1990 [GB] United Kingdom ................. 9027433

[51] Int. Cl.$^6$ ..................... A61K 31/44; G07D 211/46

[52] U.S. Cl. ..................................... 514/299; 514/934; 546/112; 546/138; 546/183

[58] Field of Search ................ 514/299, 934; 546/112, 546/138, 183

[56] References Cited

U.S. PATENT DOCUMENTS

| | | | |
|---|---|---|---|
| 4,751,236 | 6/1988 | Mishniot et al. | 514/428 |
| 4,757,088 | 7/1988 | Haines et al. | 514/563 |
| 4,760,079 | 7/1988 | Baldone | 514/642 |
| 4,782,065 | 11/1988 | Albrecht et al. | 514/299 |
| 4,800,081 | 1/1989 | Albrecht et al. | 424/129 |
| 5,004,746 | 4/1991 | Liu et al. | 514/299 |
| 5,017,563 | 5/1991 | Liu et al. | 514/27 |

FOREIGN PATENT DOCUMENTS

| | | |
|---|---|---|
| 0309952 | 5/1989 | European Pat. Off. . |
| 227566 | 9/1986 | Japan . |

OTHER PUBLICATIONS

Taylor, et al., Antiviral Research, vol. 10(1-3):11-26 (Nov. 1988).

Montalvo, et al., J. of Virology, vol. 61(9):2877-2884 (Sep. 1987).

Schlesinger, et al., Virus Research, vol. 2(2):139-149 (Mar. 1985).

Schulhafer, et al., In Vivo, vol. 3(2):61-78 (1989).

Liu, et al., Tetrahedron Letters, vol. 31(20):2829-2832 (1990).

The Merck Manual of Diagnosis and Therapy, 1987, R. Berkow, et al. (eds), pp. 180-183, Merck & Co., Inc., Rahway, N.J.

Hohenschutz, et al., Chem Abs. 95(23), 204246f, Dec. 7, 1981.

Dreyer, D. L., et al., J. Chem. Ecol., 11(8), 1045-51 (1985).

Campbell, Chem. Abs. 107(23), 215128m, Dec. 7, 1987.

Sunkara, P. S., et al. Society for Complex Carbohydrates, 17th Annual Mtg., San Antonio, Texas, Glycosidse inhibitors as Antivirals Against Human Immunodeficiency Virus (HIV) (1986).

Armstrong, Sue, Tree Compounds May Strip the Virus of Its Powers, New Scientist No. 1640, p. 23, 1988.

Saul et al., Chem Abs. 102(15), 126770u, Apr. 15, 1985.

Saul et al., Chem Abs. 98(17), 139631y, Apr. 25, 1983.

Palmarczyk, Chem. Abs. 103(3), 20519z, Jul. 22, 1985.

Chambers, J. P. Chem. Abs. 105(15), 129836t, Oct. 13, 1986.

Fiumara, Nicholas; Herpes Simplex, Varicella, and Herpes Zoster (Upjohn Pamphlet), pp. 8-28 (1986).

Fiumara, Nicholas, Herpes Simplex, Varicella, and Herpes Zoster, (Upjohn Pamphlet). (1987).

Hiroyuki, et al., Chem Abs. 105(3), 24481v, Jul. 21, 1986.

Bernotas, et al, Chem Abs. 100(23), 192129b, Jun. 4, 1984.

Hohenschutz, et al., Phytochemistry, vol. 20(4):811-814 (1981).

*Primary Examiner*—Johann Richter
*Assistant Examiner*—Catherine S. Kilby Scalzo
*Attorney, Agent, or Firm*—Kenneth J. Collier

[57] ABSTRACT

Certain Castanospermine ester derivatives of the formula:

(Abstract continued on next page.)

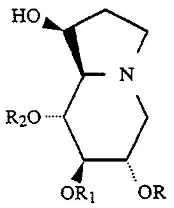

wherein R, $R_1$ and $R_2$ are each independently hydrogen, $C_{1-14}$ alkanoyl, $C_{1-14}$ alkenoyl, cyclohexanecarbonyl, $C_{1-8}$ alkoxyacetyl,

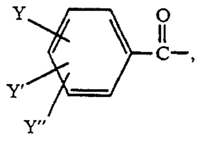

naphthalenecarbonyl optionally substituted by methyl or halogen; phenyl ($C_{2-6}$ alkanoyl) wherein the phenyl is optionally substituted by methyl or halogen; cinnamoyl; pyridinecarbonyl optionally substituted by methyl or halogen; dihydropyridine carbonyl optionally substituted by $C_1$–$C_{10}$ alkyl; thiophenecarbonyl optionally substituted by methyl or halogen; or furancarbonyl optionally substituted by methyl or halogen; Y is hydrogen, $C_{1-4}$ alkyl, $C_{1-4}$ alkoxy, halogen, trifluoromethyl, $C_{1-4}$alkylsulfonyl, $C_{1-4}$ alkylmercapto, cyano or dimethylamino; Y' is hydrogen, $C_{1-4}$ alkyl, $C_{1-4}$ alkoxy, halogen or it is combined with Y to give 3,4-methylenedioxy; Y'' is hydrogen, $C_{1-4}$ alkyl, $C_{1-4}$ alkoxy or halogen; with R, $R_1$ and $R_2$ being selected in such a way that at least one of them, but not more than two of them, is hydrogen; are disclosed to be effective in treating diseases caused by Herpes Simplex Virus (HSV) Types 1 and 2.

17 Claims, No Drawings

ANTI-HERPES CASTANOSPERMINE ESTERS

CROSS-REFERENCE TO RELATED APPLICATION

This is a continuation of application Ser. No. 07/808,150, filed Dec. 16, 1991 now abandoned.

This invention relates to the use of certain castanospermine esters in the treatment of diseases caused by Herpes Simplex Virus (HSV) Types 1 and 2.

BACKGROUND OF THE INVENTION

Research worldwide is currently underway to develop treatments and cures for Herpes Simplex Virus (HSV) Types 1and 2. Both HSV Type 1 and 2 show a predilection for infection of the ectodermal tissues wherein such infections by the virus cause lesions in the skin, oral cavity, vagina, conjunctiva, and the nervous system. Generally, infection by HSV Type 1 (HSV1) is associated with oral, facial and ocular lesions. Infection by HSV Type 2 (HSV2) generally results in genital and anal lesions. HSV infections left untreated often lead to blindness, neonatal deaths, and encephalitis. HSV Type 2 infections are at an epidemic portion in the US from venereal transmission. Greater than some twenty million persons are presently afflicted with the disease in this country with new cases and recurrences exceeding half a million annually. The annual cost of HSV infections results in a substantial economic loss to diagnose and treat. Epidemiological control of HSV is poor because the majority of the population, up to 90%, has been exposed to the virus.

Man serves as the natural host for HSV Type 1 and 2 infections whereby the virus is transmitted during close personal contact. Initial or primary infections by HSV Types 1 and 2 are contracted through breaks in the mucus membrane. In the healthy carrier the virus can be isolated in the tears, saliva, vaginal and other secretions, even during the absence of overt disease. From the mucus membrane they are able to replicate and spread to the regional lymph nodes. Occasionally these viruses can infect cells of the haemopoietic system and cause viremia.

Part of the difficulty to treat HSV infections results from the ability of these viruses to persist in a latent, or quiescent form. When the primary infection subsides or recedes, the virus generally resides in a latent form in the sensory nerve ganglia which innervate the site of primary infection. In ocular or oral infections with HSV Type 1, the virus generally resides in the trigeminal ganglia. In HSV Type 2 the viruses generally resides in the sacral ganglia serving the genitalia and lower abdoman. The determinative period of latency of the HSV virus is unknown, other than this period can be upset by heat, cold, sunlight, hormonal and emotional disturbances, or by immunosuppressive agents, resulting generally in a recurrent infection.

Treatment of HSV infections have largely been ineffective. A number of strategies to stop the virus have been developed. These agents generally inhibit any one of a number of specific viral functions such as (1) adsorption, (2) uncoating, (3) transcription, (4) protein synthesis, (5) nucleic acid replication, (6) maturation, and (7) release.

Most of the antiviral agents thus far used to treat HSV infections have been compounds that interfere with vital DNA. These compounds include Idoxuridine, Cytosine Arabinoside, Adenine Arabinoside, Trifluorothymidine and Acyclovir. Such agents also interfere with similar host functions which results in general problems with cell toxicity and systemic use in humans. Presently, Acyclovir is the preferred medication to treat infections with HSV1 and HSV2 due to its potent antiviral effect and negligable toxicity. Poor solubility at high dosage and the emergence of drug-resistant viruses, however, limit the use of this drug.

A number of RNA and DNA containing viruses have envelopes into which virus-coded glycopeptides are incorporated. HSV is one of the enveloped viruses. Infection of a host cell by enveloped viruses initially relies on the interaction of various receptors on the host cell surface with the envelope glycoproteins of the vital membrane. Subsequently the virus and cell membranes fuse and the virion contents are released into the host cell cytoplasm. The glycoprotein containing envelope of the virus plays an important role in both the initial interaction of the virion and the host cell and in the later fusion of the viral and host cell membranes. The viral envelope seems to be derived from the cellular membrane, but the specificity is due to the viral encoded glycopeptides. Therefore, an inhibitor capable of interfering with the formation of the virus-specific membranes may prevent formation of infectious progeny virus.

Interference with the formation of the viral envelope glycoprotein could prevent the initial virus-host cell interaction or subsequent fusion or could inhibit vital replication by preventing the required synthesis of glycoproteins to produce infectious virions. It has been recently reported that the nonspecific inhibitors of glycosylation, 2-deoxy-D-glucose and β-hydroxy-norvaline inhibit expression of HIV glycoproteins and block the formation of syncytia. H. A. Blough, et al., *Biochemical and Biophysical Research Communications,* 141(1), 33–38 (1986). Furthermore, 2-deoxy-D-glucose is also active against HSV and has shown efficacy in the treatment of Herpes infections in man. In another report, the glycosylation inhibitor 2-deoxy-2-fluoro-D-mannose was found to exhibit antiviral activity against influenza infected cells by preventing the glycosylation of viral membrane protein (W. McDowell, et al., *Biochemistry,* 24(27), 8145–52 (1985)). This report also studied the antiviral activity of 2-deoxyglucose and 2-deoxy-2-fluoroglucose and found that each inhibit viral protein glycosylation by a different mechanism. Many other known glycosylation inhibitors are found to have no antiviral activity. Thus the antiviral activity of inhibitors of glycosylation per se are quite unpredictable.

Inhibitors of the processing enzymes involved in the shaping of the oligosaccharide portion of the viral glycoprotein may provide more selectivity in their mechanism of action. The applicants' have found that certain compounds derived from Castanospermine are effective against the viral processing enzyme and therefore are potentially useful in the treatment of HSV infections.

Castanospermine is an alkaloid, originally isolated from the seeds of *Castanospermum australe* having the following formula:

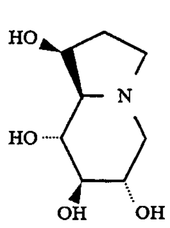

Systematically, this compound can be named in several ways as follows: [1S-(1α, 6β, 7α, 8β, 8aβ)]-octahydro-1,6,7,8-indoli-zinetetrol or [1S,(1S,6S,7R,8R,8aR)-1,6,7,8-tetrahydroxy-indolizidine or 1,2,4,8-tetradeoxy-1,4,8-nitrilo-L-*glycero*-D-*galacto*-octitol. The term "castanospermine" or the first systematic name will be used in the discussion below.

The isolation of this compound and the determination of its structure has been described by L. D. Hohenshutz,. et al., *Phytochemistry,* 20, 811 (1981). As part of his study of castanospermine, Hohenshutz obtained castanospermine tetraacetate by the reaction of castanospermine with a very large excess of acetic anhydride but there is no suggestion of any other esters of castanospermine in the article.

The applicants have now discovered that certain esters of castanospermine that are potent inhibitors of the glycoprotein processing enzymes that are considered to be a requiste to correctly synthesize viral glycoproteins. The castanospermine esters are therefore considered to be useful in the treatment of various HSV infections.

SUMMARY OF THE INVENTION

The present invention is directed to certain ester derivatives of castanospermine. More particularly, it is directed to compounds having the following formula (1) for treatment of Herpes viral infections:

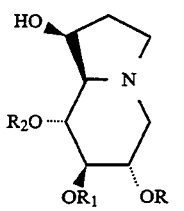

(1)

wherein R, $R_1$ and $R_2$ are independently hydrogen, $C_{1-14}$ alkanoyl, $C_1$–$C_{14}$ alkenoyl, cyclohexanecarbonyl, $C_{1-6}$ alkoxyacetyl,

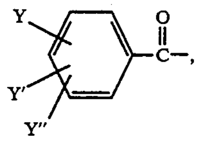

naphthalenecarbonyl optionally substituted by methyl or halogen; phenyl($C_{2-6}$ alkanoyl) wherein the phenyl is optionally substituted by methyl or halogen; cinnamoyl; pyridinecarbonyl optionally substituted by methyl or halogen; dihydropyridine carbonyl optionally substituted by $C_{1-10}$ alkyl; thiophenecarbonyl optionally substituted by methyl or halogen; or furancarbonyl optionally substituted by methyl or halogen; Y is hydrogen, $C_{1-4}$ alkyl, $C_{1-4}$ alkoxy, halogen, trifluoromethyl, $C_{1-4}$ alkylsulfonyl, $C_{1-4}$ alkylmercapto, cyano or dimethylamino; Y' is hydrogen, $C_{1-4}$ alkyl, $C_{1-4}$ alkoxy, halogen or it is combined with Y to give 3,4-methylenedioxy; Y" is hydrogen, $C_{1-4}$ alkyl, $C_{1-4}$ alkoxy or halogen; with R, $R_1$ and $R_2$ being selected in such a way that at least one of them, but not more than two of them, is hydrogen; or a pharmaceutically acceptable salt of these compounds.

DETAILED DESCRIPTION OF THE INVENTION

The $C_{1-14}$ alkanoyl groups referred to above can be straight- or branched-chain or cyclic and can be exemplified by formyl, acetyl, propionyl, butyryl, isobutyryl, cyclopropanecarbonyl, hexanoyl, octanoyl and decanoyl. The $C_{1-14}$ alkenoyl groups referred to above can be straight- or branched-chain or cyclic but have at least one carbon-carbon double bond as exemplified, propenoyl, butenoyl, isobutenoyl, hexenoyl, octenoyl and decenoyl. The $C_{1-6}$ alkoxyacetyl referred to above can be methoxy-acetyl, ethoxyacetyl and butoxyacetyl. The halogens referred to above can be exemplified by fluorine, chlorine, bromine or iodine. The $C_{2-6}$ alkanoyl groups referred to above can be exemplified by acetyl, propionyl, butyryl, isobutyryl, and hexanoyl. The $C_{1-4}$ alkyl groups referred to above, whether alone or as part of an alkoxy, an alkylsulfonyl or an alkyl-mercapto group, can be straight- or branched-chain alkyl groups containing up to 4 carbon atoms. Examples of various such groups are methyl, ethyl, propyl, butyl, methoxy, ethoxy, butoxy, methylsulfonyl, ethylsulfonyl, methylmercapto and ethylmercapto. The phenyl ($C_{2-6}$ alkanoyl) groups referred to above can be exemplified by benzeneacetyl and benzenepropionyl. The various naphthalenecarbonyl, pyridinecarbonyl, thiophenecarbonyl and furancarbonyl groups referred to above include the various position isomers and these can be exemplified by naphthalene-1-carbonyl, naphthalene-2-carbonyl, nicotinoyl, isonicotinoyl, N-methyl-dihydropyridine- 3-carbonyl, thiophene-2-carbonyl, thiophene-3-carbonyl, furan-2-carbonyl and furan-3-carbonyl. The naphthalene, pyridine, thiophene and furan groups can be optionally further substituted as indicated above.

The expression "a pharmaceutically acceptable acid addition salt" is intended to apply to any non-toxic organic or inorganic acid addition salt of the base compounds. Illustrative inorganic acids which form suitable salts include hydrochloric, hydrobromic, sulfuric, and phosphoric acids and acid metal salts such as sodium monohydrogen orthophosphate and potassium hydrogen sulfate. Illustrative organic acids which form suitable salts include the mono, di, and tricarboxylic acids. Illustrative of such acids are, for example, acetic, glycolic, lactic, pyruvic, malonic, succinic, glutaric, fumaric, malic, tartaric, citric, ascorbic, maleic, hydroxymaleic, benzoic, hydroxybenzoic, phenylacetic, cinnamic, salicylic, and 2-phenoxybenzoic acids. Other organic acids which form suitable salts are the sulfonic acids such as methane sulfonic acid and 2-hydroxyethane sulfonic acid. These salts and the base compounds can exist in either a hydrated or a substantially anhydrous form. The acid salts are prepared by standard techniques such as by dissolving the free base in aqueous or aqueous-alcohol solution or other suitable solvent containing the appropriate acid and isolating by evaporating the solution, or by reacting the free base in an organic solvent in which case the salt separates directly or can be obtained by concentration of the solution. In general the acid addition salts of the compounds of this invention are crystalline materials which are soluble in water and various hydrophilic organic solvents and which in comparison to their free base forms, demonstrate higher melting points and an increased solubility.

Preferred compounds of the present invention are those wherein R, $R_1$ and $R_2$ are 1 or 2 alkanoyl, alkenoyl, or benzoyl groups with the benzoyl substituted by Y, Y' and Y'' as described above, especially a $C_{1-4}$ alkanoyl or a benzoyl optionally substituted with an alkyl or halogen. More preferred are those compounds of formula 1 wherein one of R, $R_1$ and $R_2$ is alkanoyl or benzoyl, especially a $C_{1-8}$ alkanoyl, $C_{1-8}$ alkenoyl, or a benzoyl optionally substituted with an alkyl or halogen, and the others are hydrogens. Even more preferred are those compounds of formula 1 wherein one of R, $R_1$ and $R_2$ is a $C_{1-8}$ alkanoyl, $C_{1-8}$ alkenoyl, or a benzoyl optionally substituted with an alkyl or halogen, especially a methyl, bromo, chloro, or fluoro group, and the others are hydrogens. Most preferred are those compounds of formula 1 wherein $R_1$ is a $C_{1-8}$ alkanoyl, $C_{1-8}$ alkenoyl, or benzoyl optionally substituted with an alkyl or halogen, especially a methyl, bromo, chloro, or fluoro group, most especially a methyl, bromo, chloro, or fluoro group at the para position, and wherein R and $R_2$ are each a hydrogen.

The esters of the present invention are prepared by the reaction of castanospermine with an appropriate acid chloride or anhydride in an inert solvent. The halide can be a chloride or bromide and the anhydride includes mixed anhydrides. The relative amount of the acid halide or anhydride used, the relative amount of solvent, the temperature and the reaction time are all controlled so as to minimize the number of hydroxy groups that will be acylated. Thus, only a limited excess of the acid derivative is used, which means up to about a three-fold excess of the acylating agent. Use of a solvent in relatively large amounts, serves to dilute the reactants and hold down the amount of higher acylated products that form. The solvent used is preferably one that will dissolve the reactants used without reacting with them. It is further preferable to carry out the reaction in the presence of a tertiary amine which will react with and remove any acid formed during the course of the reaction. The tertiary amine can be added to the mixture or it can itself be used in excess and serve as the solvent. Pyridine is a preferred solvent in this regard. As indicated above, the time and the temperature are likewise controlled to limit the amount of acylation that takes place. Preferably, the reaction is carried out with cooling in an ice-bath for a period of about 16 hours to give the monoesters with the reaction time extended to a longer period, such as 7 days, if diesters are desired. The reaction can actually be carried out at higher temperatures and, in fact, heating can be used as long as the various factors involved are properly controlled. The fact of the matter is, when the reaction is carried out as described, the final reaction mixture will still contain a considerable amount of unreacted castanospermine. This unreacted material can be recovered from the reaction mixture and recycled in subsequent reactions and thus increase the overall amount of castanospermine converted to ester. This recycling is particularly important when the reaction is carried out under conditions which would favor the isolation of monoesters.

The procedures as described above will generally give 6-or 7-monoesters or 6,7- or 6,8-diesters. Other isomers can be obtained by appropriate use of blocking groups. Thus, for example, castanospermine can be reacted with 2-(dibromomethyl)benzoyl chloride to give the 6,7-diester. This diester is then reacted with an appropriate acid halide or anhydride to give the corresponding 8-ester. The two protecting groups are then readily removed by conversion of the two dibromomethyl groups to formyl (using silver perchlorate and 2,4,6-collidine in aqueous acetone) followed by hydrolysis of the formylbenzoic acid ester obtained using morpholine and hydroxide ion. The indicated procedure can be used in a similar way to give diester isomers.

Alternatively, the 1,8-O-isopropylidenecastanospermine or 1,8-cyclohexylidenecastanospermine, the reaction of this material with an acid chloride in a standard esterification procedure favors the formation of the 6-ester almost exclusively. The isopropylidene or cyclohexylidene group is then removed by treatment with an acid such as 4-toluenesulfonic acid. The starting ketal compounds are themselves obtained form castanospermine 6,7-dibenzoate. This dibenzoate is reacted with 2-methoxypropene or 1-methoxycyclohexene and acid to introduce the 1,8-O-isopropylidene or 1,8-O-cyclohexylidene group and the two benzoate ester groups are removed by hydrolysis with base such as sodium hydroxide or by transesterification with sodium or potassium alkoxide as the catalyst.

Herpes virus infections

The ability of the castanospermine ester derivatives of this invention to act as anti-viral agents can be demonstrated by their ability to inhibit the growth and replication of HSV virus. Used herein the term "a method of treating a Herpes viral infection" refers a patient who as been in infected with the Herpes virus, either type 1 or type 2, and administering to said patient a virally effective amount of a compound of formula (1). Futhermore, it is also understood that the term "viral infection" refers to any state or condition characterized by the virus residing in the cells or body of said patient.

Antiviral activity of the compounds of formula (1) can assessed by the plaque-reduction assay as previously described by Tyms et al., J. Antimicrobial Chemotherapy, 8, 65–72 (1981). Briefly, human embryonic fibroblast cells (MRC5) were cultured in 24-well tissue culture trays in the presence of Eagles' minimum essential medium (MEM) supplemented with 10% fetal calf serum. When cell monolayers were semi-confluent, they were inoculated with 30–50 plaque-forming units of HSV2 strain HG52 or HSV1 strain 17*i* (Davison & Wilkie, J. General Virology, 55, 315–331 (1981). At the end of an adsorption period of one hour at room temperature, infected monolayers were overlayed with MEM containing 2% fetal calf serum, 0.5% low-temperature gelling agarose and the antiviral compound at a range of concentrations. After 3 days incubation, cells were fixed in 10% formalin in saline and subsequently stained with 0.3% methylene blue. Dose-response lines were plotted from the mean number of plaques present versus the log of the concentration of the compound. The 50% effective dose (ED50) was computed after linear regression analysis.

The antiviral activities of various compounds of this invention are tabulated in Table 1.

TABLE 1

| INHIBITORY CONCENTRATION OF VARIOUS CASTANOSPERMINE ESTER DERIVATIVES OF FORMULA 1 | | | |
|---|---|---|---|
| Reference No. | CHEMICAL NAME | $ED_{50}$ (vg/ml) HSVI | $ED_{50}$ (vg/ml) HSVII |
| MDL 28,574 | [1S-(1α,6β,7α,8β,8aβ)]-octahydro-1,6,7,8-indolizinetetrol 6-butanoate | ≦75 | ≦22 |
| MDL 43,305 | [1S-(1α,6β,7α,8β,8aβ)]-octahydro-1,6,7,8-indolizinetetrol 6-benzoate | — | ≦20 |
| MDL 29,204 | [1S-(1α,6β,7α,8β,8aβ)l-octahydro-1,6,7,8-indolizinetetrol 6-(4-methylbenzoate) | — | ≦20 |
| MDL 29,513 | [1S-(1α,6β,7α,8β,8aβ)]-octahydro-1,6,7,8-indolizinetetrol 6-(3-hexenoate) | ≦5 | ≦5 |
| MDL 29,797 | [1S-(1α,6β,7α,8β,8aβ)]-octahydro-1,6,7,8-indolizinetetrol 6-octanoate | ≦10 | ≦5 |

Applicants consider the use of the castanospermine ester derivatives of this invention to treat HSV infections in humans to be of most importance. The term "patient" used herein is taken to mean mammals such as primates, including humans, sheep, horses, cattle, pigs, dogs, cats, rats and mice. The applicants refer to the term Herpes viral infection used herein to mean infections caused by either by the Herpes Type I Virus or the Herpes Type 2 Virus.

The amount of the castanospermine ester derivative of formula (1) to be administered can vary widely according to the particular dosage unit employed, the period of treatment, the age and sex of the patient treated, the nature and extent of the disorder treated, and the particular castanospermine ester derivative selected. Moreover the castanospermine ester derivative can be used in conjunction with other agents known to be useful in the treatment of HSV infections and agents known to be useful to treat the symptoms of and complications associated with diseases and conditions caused by virus. The anti-Herpes virally effective amount of a castanospermine ester derivative of formula 1 to be administered will generally range from about 15 mg/kg to 500 mg/kg. A unit dosage may contain from 25 to 500 mg of the castanospermine ester derivative, and can be taken one or more times per day. The castanospermine ester derivative can be administered with a pharmaceutical carrier using conventional dosage unit forms either orally, parenterally, or topically.

The preferred route of administration is oral administration. For oral administration the castanospermine ester derivative can be formulated into solid or liquid preparations such as capsules, pills, tablets, troches, lozenges, melts, powders, solutions, suspensions, or emulsions. The solid unit dosage forms can be a capsule which can be of the ordinary hard- or soft-shelled gelatin type containing, for example, surfactants, lubricants, and inert fillers such as lactose, sucrose, calcium phosphate, and cornstarch. In another embodiment the compounds of this invention can be tableted with conventional tablet bases such as lactose, sucrose, and cornstarch in combination with binders such as acacia, cornstarch, or gelatin, disintegrating agents intended to assist the break-up and dissolution of the tablet following administration such as potato starch, alginic acid, corn starch, and guar gum, lubricants intended to improve the flow of tablet granulations and to prevent the adhesion of tablet material to the surfaces of the tablet dies and punches, for example, talc, stearic acid, or magnesium, calcium, or zinc stearate, dyes, coloring agents, and flavoring agents intended to enhance the aesthetic qualities of the tablets and make them more acceptable to the patient. Suitable excipients for use in oral liquid dosage forms include diluents such as water and alcohols, for example, ethanol, benzyl alcohol, and the polyethylene alcohols, either with or without the addition of a pharmaceutically acceptably surfactant, suspending agent, or emulsifying agent.

The castanospermine ester derivatives of this invention may also be administered parenterally, that is, subcutaneously, intravenously, intramuscularly, or interperitoneally, as injectable dosages of the compound in a physiologically acceptable diluent with a pharmaceutical carrier which can be a sterile liquid or mixture of liquids such as water, saline, aqueous dextrose and related sugar solutions, an alcohol such as ethanol, isopropanol, or hexadecyl alcohol, glycols such as propylene glycol or polyethylene glycol, glycerol ketals such as 2,2-dimethyl-1,3-dioxolane-4-methanol, ethers such as poly(ethylene-glycol) 400, an oil, a fatty acid, a fatty acid ester or glyceride, or an acetylated fatty acid glyceride with or without the addition of a pharmaceutically acceptable surfactant such as a soap or a detergent, suspending agent such as pectin, carhomers, methylcellulose, hydroxypropylmethylcellulose, or carboxymethylcelluiose, or emulsifying agent and other pharmaceutically adjuvants. Illustrative of oils which can be used in the parenteral formulations of this invention are those of petroleum, animal, vegetable, or synthetic origin, for example, peanut oil, soybean oil, sesame oil, cottonseed oil, corn oil, olive oil, petrolatum, and mineral oil. Suitable fatty acids include oleic acid, stearic acid, and isostearic acid. Suitable fatty acid esters are, for example, ethyl oleate and isopropyl myristate. Suitable soaps include fatty alkali metal, ammonium, and triethanolamine salts and suitable detergents include cationic detergents, for example, dimethyl dialkyl ammonium halides, alkyl pyridinium halides, and alkylamines acetates; anionic detergents, for example, alkyl, aryl, and olefin sulfonates, alkyl, olefin, ether, and monoglyceride sulfates, and sulfosuccinates; nonionic detergents, for example, fatty amine oxides, fatty acid alkanolamides, and polyoxyethylenepolypropylene copolymers; and amphoteric detergents, for example, alkyl-beta-aminopropionates, and 2-alkylimidazoline quarternary ammonium salts, as well as mixtures. The parenteral compositions of this invention will typically contain from about 0.5 to about 25% by weight of the castanospermine ester derivative of formula 1 in solution. Preservatives and buffers may also be used advantageously. In order to minimize or eliminate irritation at the site of injection, such compositions may contain a non-ionic surfactant having a hydrophile-lipophile balance (HLB) of from about 12 to about 17. The quantity of surfactant in such formulations ranges from about 5 to about 15% by weight. The surfactant can be a single component having the above HLB or can be a mixture of two or more components having the desired HLB. Illustrative of surfactants used in parenteral formulations are the class of polyethylene sorbitan fatty acid esters, for example, sorbitan monooleate and the high molecular weight adducts of ethylene oxide with a hydrophobic base, formed by the condensation of propylene oxide with propylene glycol.

The castanospermine ester derivatives of this invention may also be administered topically, and when done so the carrier may suitably comprise a solution, ointment or gel base. The base, for example, may comprise one or more of the following: petrolatum, lanolin, polyethylene glycols, bee wax, mineral oil, diluents such as water and alcohol, and emulsifiers and stabilizers. Topical formulations may contain a concentration of the castanospermine ester or it's pharmaceutical salt from about 0.1 to about 10% w/v (weight per unit volume).

EXAMPLE 1

A slurry of 4.0 g of castanospermine in 140 ml of pyridine was stirred at room temperature for 30 minutes until essentially all of the solids had dissolved. The solution was cooled to 0° C. in an ice/water bath, and a solution of 5.85 ml of benzoyl chloride in 15 ml of pyridine was added dropwise over 15 minutes under nitrogen. After the addition, the reaction was stirred at 8° C. overnight.

The reaction mixture was partitioned between 225 ml methylene chloride and 300 ml water. The organic layer was separated and the aqueous layer extracted with two 225-ml portions of methylene chloride. The combined organic layers were washed successively with 150 ml of 0.5N hydrochloric acid, saturated sodium carbonate, water and saturated sodium chloride solutions, and then dried over sodium sulfate. Evaporation of solvents under reduced pressure gave 2.9 g of a tan glassy residue.

This material was slurried in chloroform and a white precipitate formed. These solids were isolated to afford 910 mg of a white powder. Thin layer chromatography (85:15, ethyl acetate:methanol) analysis showed the material to be composed of two components (Rf 0.33 and Rf 0.26). The solid mixture was slurried in 45 ml of 4:1 ethyl acetate:methanol and filtered. The residue was dried *in vauco* to provide 350 mg of [1S-(1α, 6β, 7α, 8β, 8aβ)]-octahydro-1,6,7,8-indolizinetetrol 6-benzoate as a white powdery solid melting at about 233°-236° C., with decomposition. This corresponded to the less polar component of the mixture. NMR (DMSO-$d_6$) δ 1.5-2.2 (m, 5H), 2.9-3.6 (m, 4H), 4.1 (m, 1H, $C_1$-H), 4.3 (d, 1H, -OH) 4.7 (d, 1H, -OH), 4.8 (sextet, 1H, $C_6$-H), 5.1 (d, 1H, -OH), 7.6-8.1 (m, 5H, aryl). MS (CI-$CH_4$) 294 ($MH^+$), 276 ($MH^+$-$H_2O$), 172 ($MH^+$-$PhCO_2H$).

The filtrate from above was condensed and fractionated by preparative thin layer chromatography (silica gel, 80:20, ethyl acetate:methanol) to provide 120 mg of the more polar component, [1S-(1α, 6β, 7α, 8β, 8aβ)]-octahydro-1,6,7,8-indolizinetetrol 7-benzoate as a white powdery solid melting at about 200°-202° C. NMR (DMSO-$d_6$+$D_2O$) 1.5-2.2 (m, 5H), 2.9-3.1 (m, 2H), 3.6-3.8 (m, 2H), 4.1 (m, 1H, $C_1$-M), 4.8 (t, 1H, $C_7$-H), 7.4-8.1 (m, 5H, aryl). MS (CI-$CH_4$) 294 ($MH^+$), 276 ($MH^+$-$H_2O$), 172 ($MH^+$-$PhCO_2H$). This compound has the following structural formula:

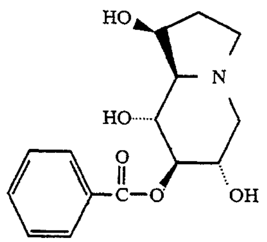

EXAMPLE 2

Castanospermine (1.89 g) was added to a stirred solution of 10 ml of pyridine and cooled to 0° C. in an ice bath. Benzoyl chloride, 3.0 g, was added dropwise to the mixture and the resulting suspension was kept at 0°-4° C. for 7 days. Water, 10 ml, was added and the mixture was evaporated to dryness *in vacuo*. The resulting residue was redissolved in 1:1 water:ethyl acetate (100 ml) and the phases were separated. The aqueous layer was extracted again with 100 ml of ethyl acetate. The organic extracts were combined and concentrated to a syrup which was shown to be a mixture of two major components by thin layer chromatography (1:1 ethyl acetate:hexane, silica gel, Rf=0.42 and Rf=0.11). The mixture was separated by preparative high pressure liquid chromatography (silica gel, 1:1 ethyl acetate:hexane) to provide 1.9 g (48%) of the more polar [1S-(1α, 6β, 7α, 8β, 8aβ)]-octahydro-1,6,7,8-indolizinetetrol 6,7-dibenzoate as a dry foam melting at about 79°-81° C. NMR (DMSO-$d_6$/$D_2O$) δ 1.5-2.3 (m, 5H), 3.0-3.4 (m, 2H), 3.9 (t, 1H), 4.2 (m, 1H, $C_1$-M), 5.15 (m, 1H, $C_6$-H), 5.3 (t, 1H, $C_7$-H), 7.4-8.0 (m, 10H, aryl). MS (FAB-Xe) 398 ($MH^+$), 380 ($MH^+$-$H_2O$), 276 ($MH^+$-$PhCO_2H$). The less polar component (Rf=0.42) was isolated as a dry foam melting at about 75°-78° C. which was [1S-(1α, 6β, 7α, 8β, 8aβ)]-octahydro-1,6,7,8-indolizinetetrol 6,7,8-tribenzoate.

EXAMPLE 3

When the procedure of Example 1 was repeated using castanospermine and the appropriate acid chloride, the following compounds were obtained:

[1S-(1α, 6β, 7α, 8β, 8aβ]-octahydro-1,6,7,8-indolizinetetrol 6-(4-fluorobenzoate) melting at about 216°-218° C.;

[1S-(1α, 6β, 7α, 8β, 8aβ]-octahydro-1,6,7,8-indolizine-tetrol 6-(4-fluorobenzoate) melting at about 190°-193° C.;

[1S-(1α, 6β, 7α, 8β, 8aβ)]-octahydro-1,6,7,8-indolizine-tetrol 7-(2,4-dichlorobenzoate) melting at about 179°-181° C.;

[1S-(1α, 6β, 7α, 8β, 8aβ)]-octahydro-1,6,7,8-indolizine-tetrol 6-(4-bromobenzoate) melting at about 234°-235° C.;

[1S-(1α, 6β, 7α, 8β, 8aβ)]-octahydro-1,6,7,8-indolizine-tetrol 6-(4-methoxybenzoate) melting at about 221°-224° C.

EXAMPLE 4

When the procedure of Example 2 was repeated using castanospermine and 4-fluorobenzoyl chloride, the product obtained was [1S-(1α, 6β, 7α, 8β, 8a β)]-octahydro-1,6,7,8-indolizinetetrol 6,7-bis(4-fluorobenzoate) melting at about 82°-84° C.

EXAMPLE 5

To a suspension of 3 g of castanospermine in 30 ml of pyridine at 0° C. was added dropwise a solution of 3 g of 4-methylbenzoyl chloride. After the addition, the mixture was allowed to warm to room temperature and then heated at 55° C. for 24 hours. The reaction mixture was diluted with 10 ml of water and evaporated to dryness in vacuo. The resulting residue was stirred in 150 ml of a 1:2 mixture of water:methylene chloride. The insoluble material was separated by filtration to provide an amorphous off-white solid which was dissolved in 60 ml of hot methanol, treated with 0.5 g of activated charcoal and filtered. The colorless liltrate was cooled to give colorless crystals of [1S-(1α, 6β, 7α, 8β, 8αβ)]-octahydro-1,6,7,8-indolizine-tetrol 6-(4-methylbenzoate) melting at about 255°–258° C. with decomposition (580 mg, 12% yield).

The two-phase water/methylene chloride mixture obtained above was evaporated to dryness and the residue was dissolved in 50 ml of a 1:2 mixture of methanol:ethyl acetate. The solution was fractionated by preparative high pressure liquid chromatography (silica gel, 9:1 ethyl acetate:methanol) and fractions containing the more polar component (i.e., more polar than the 6-ester obtained in the preceding paragraph) were collected and evaporated in vacuo to provide a colorless solid which was [1S-(1α, 6β, 7α, 8β, 8αβ)]-octahydro-1,6,7,8-indolizinetetrol 7-(4-methylbenzoate) melting at about 220°–223° C. with decomposition (210 mg, 4% yield).

EXAMPLE 6

When the procedure of Example 5 is repeated using castanospermine and the appropriate acid chloride, the following esters are obtained:

6-(3-Methylbenzoate);
7-(3-Methylbenzoate);
6-(3-Trifluoromethylbenzoate);
6-(4-Methylsulfonylbenzoate);
6-(4-Methylmercaptobenzoate);
6-(3-Cyanobenzoate);
6-(4-Dimethylaminobenzoate);
6-(3,4-Methylenedioxybenzoate);
6-(3,4,5-Trichlorobenzoate);
7-(3,4,5-Trichlorobenzoate);
6-(2,4-Dimethylbenzoate);
6-(2-Naphthalenecarboxylate);
7-(2-Naphthalenecarboxylate);
6-(4-Methyl-2-naphthalenecarboxylate);
6-(Benzeneacetate);
7-(Benzeneacetate);
6-(4-Chlorobenzeneacetate);
6-(Benzenepropionate);
6-(Cinnamate);
7-(Cinnamate);
6-(Cyclohexanecarboxylate);
6-Nicotinoate;
6-Isonicotinoate;
6-(2-Thiophenecarboxylate);
6-(2-Furancarboxylate) melting at about 209°–212° C.

EXAMPLE 7

Castanospermine (350 mg) was added to 5 ml of pyridine and stirred under nitrogen at room temperature. Butyric anhydride (0.97 g) was added dropwise and the mixture was kept at room temperature for 24 hours. The reaction mixture was evaporated to dryness in vacuo to leave a syrupy residue. The residue was dissolved in ether and a colorless solid precipitated when pentane was added. Recrystallization of the solid from a mixture of ether and petroleum ether gave colorless needles of [1S-(160, 6β, 7α, 8β, 8αβ)]-octahydro-1,6,7,8-indolizinetetrol 6,8-dibutanoate melting at about 110°–111° C. (22 mg, 4% yield). NMR (CDCl$_3$) δ 3.7 (t, 1H, C$_7$-H) 4.1 (m, 1H, C$_1$-H) 4.85 (t, 1H, C$_8$-H), 5.0 (m, 1H, C$_6$-H). MS (CI-CH$_4$) 330 (MH+), 312 (MH+-H$_2$O).

EXAMPLE 8

When the procedure of Example 7 is repeated using acetic anhydride, propionic anhydride or caproic anhydride in place of the butyric anhydride, the corresponding 6,8-diesters are obtained.

EXAMPLE 9

To a stirred suspension of 1.5 g of castanospermine in 15 ml of pyridine cooled at 0° C. in an ice-bath was added dropwise 1.0 g of butyryl chloride. The mixture was stirred at room temperature for 3 days and added to a 1:1 mixture of water:methylene chloride (400 ml). After partitioning, the aqueous phase was concentrated in vacuo to provide an oily residue which was fractionated by radial thin layer chromatography (silica gel, 2 mm thickness plate, 2:8 methanol:chloroform) to provide 68 mg of [1S(1α, 6β, 7α, 8β, 8αβ)]-octahydro-1,6,7,8-indolizinetetrol 6-butanoate, homogeneous by thin layer chromatography (silica gel, 2:8 methanol:chloroform, Rf=0.5). Recrystallization of the product from 5:95 isopropanol:hexane gave a colorless solid melting at 113°–114° C. NMR (CDCl$_3$) δ 3.5–3.8 (2t, 2H, C$_7$-H and C$_8$-H), 4.4 (m, 1H, C$_1$-H), 4.95 (m, 1H, C$_6$-H). MS (CI-CH$_4$) 260 (MH+), 242 (MH+-H$_2$O), 172 (MH+-C$_3$H$_7$CO$_2$H).

Similarly, when the above procedure was repeated using acetyl chloride or propionyl chloride, the following mono-esters were obtained:

[1S-(1α, 6β, 7α, 8β, 8αβ)]-octahydro-1,6,7,8-indolizine-tetrol 6-acetate melting at about 188°–189° C.

[1S-(1α, 6β, 7α, 8β, 8αβ)]-octahydro-1,6,7,8-indolizine-tetrol 7-propionate melting at about 153°–155° C.

EXAMPLE 10

A mixture of 5.0 g of [1S-(1α, 6β, 7α, 8β, 8αβ)]-octahydro-1,6,7,8, -indolizinetetrol 6,7-dibenzoate hydrochloride, 100 ml of 1,2-dimethoxyethane, 22 ml 0.22 g of 4-tolunesulfonic acid monohydrate was refluxed with stirring for 1.5 hours to give a clear solution. The reaction was cooled to 25° C. and diluted with 30 ml of saturated aqueous sodium bicarbonate solution and 60 ml of water. This solution was then extracted twice with methylene chloride and the combined organic extracts were dried over magnesium sulfate and the solvent was evaporated in vauco to give a light green foam. This material was recrystallized form penatane to give [1S-(1α, 6β, 7α, 8β, 8αβ)]-1,8-O-isopropylideneoctahydro-1,6,7,8,-indolizinetetrol 6,7-dibenzoate as white crystals melting at about 132°–133° C. (78.6%) yield).

To a solution of 0.34 g of [1S-(1α, 6β, 7α, 8β, 8αβ)]-1,8-O-isopropylideneoctahydro-1,6,7,8,-indolizinetetrol 6,7-dibenzoate in 50 ml of tetrahydrofuran, at 25° C., there was added 3.1 ml of 1N aqueous sodium hydroxide in one portion. The reaction mixture was stirred for 24 hours, diluted with 10 ml of saturated brine, and extracted with four portions of methylene chloride. the combine organic extracts were dried with magnesium sulfate and the solvent was evaporated in vacuo to give

[1S-(1α, 6β, 7α, 8β, 8aβ)]-1,8-O-isopropylideneoctahydro-1,6,7,8, -indolizinetetrol as a clear glass which was used without further purification (95% yield). 1H NMR ($CDCl_3$, 300 MHz) δ 4.5 (d, 1H), 3.8 (m, 1H), 3.65 (t, 1H), 3.5 (dd, 1H), 3.25 (dd, 1H), 3.0 (m, 2H), 2.8 (m, 2H), 2.2 (m, 1H), 1.9 (m, 1H).

EXAMPLE 11

A mixture of 0.3 g of [1S-(1α, 6β, 7α, 8β, 8aβ)]-1,8-O-isopropylideneoctahydro-1,6,7,8, -indolizinetetrol, 6.0 ml of methylene chloride and 0.54 ml of triethylamine was cooled to 0° C. and 0.18 ml of benzolyl chloride was added dropwise with stirring. The reaction was then stirred at 0°-5° C. for 24 hours before dilution with 10 ml of water and 3 ml of saturated aqueous sodium bicarbonate solution. The layers were separated and the aqueous layer was extracted twice with methlene chloride. The combined organic layers were then dried over magnesium sulfate and the solvent was evaporated *in vacuo* give a crude solid product. This solid was recrystallised from ethyl acetate/pentane (1:2) to give [1S-(1α, 6β, 7α, 8β, 8aβ)]-1,8-O-isopropylideneocta-hydro-1,6,7,8,-indolizinetetrol 6-benzoate as white needles melting at about 181°-183° C. (77.9% yield).

A solution was prepared form 0.2 g of [1S-(1α, 6β, 7α, 8β, 8aβ)]-1,8-O-isopropylideneoctahydro-1,6,7,8,-indolizinetetrol 6-benzoate and 10 ml of methanol. To this solution, at 25° C., was added 0.34 g of 4-toluenesulfonic acid monohydrate in one portion. The reaction was stirred for one hour and the mixture was then diluted with 30 ml of methylene chloride, 10 ml of saturated aqueous sodium bicarbonate solution, and 10 ml of saturated brine. The layers were separated, the aqueous layer was extracted five times with methylene chloride, and the combined organic layers were dried over magnesium sulfate. The solvent was then evaporated *in vacuo* to give [1S-(1α, 6β, 7α, 8β, 8aβ)]-octahydro-1,6,7,8-indolizinetetrol 6-benzoate as a white powder melting at about 233°-235° C. with decomposition (91% yield).

Similarly, when the above procedure was repeated using 3-hexenyl chloride, octanyl chloride, pentyl chloride, or butryl chloride, the following mono-esters were obtained:

1S-(1α, 6β, 7α, 8β, 8aβ)]-octahydro-1,6,7,8-indolizine-tetrol 6-(3- hexenoate).

[1S-(1α, 6β, 7α, 8β, 8aβ)]-octahydro-1,6,7,8-indolizine-tetrol 6-octanoate melting at about 105°-106° C.

[1S-(1α, 6β,7α, 8β, 8aβ)]-octahydro-1,6,7,8-indolizine-tetrol 6-pentanoate. [1S-(1α, 6β, 7α, 8β, 8aβ)]-octahydro-1,6,7,8-indolizine-tetrol 6-butanoate melting at about 113°-114° C.

EXAMPLE 12

Tablets are prepared each having the composition:

| | |
|---|---|
| [1S-(1α,6β,7α,8β,8aβ)]-octahydro-1,6,7,8-indolizinetetrol 6-benzoate | 250 mg |
| starch | 40 mg |
| talc | 10 mg |
| magnesium stearate | 10 mg |

EXAMPLE 13

Capsules are prepared each having the composition:

| | |
|---|---|
| [1S-(1α,6β,7α,8β,8aβ)]-octahydro-1,6,7,8-indolizinetetrol 6,7-dibenzoate | 400 mg |
| talc | 40 mg |
| sodium carboxymethylcellulose | 40 mg |
| starch | 120 mg |

EXAMPLE 14

Injectable dosages forms are prepared each having the composition:

| | |
|---|---|
| [1S-(1α,6β,7α,8β,8aβ)]-octahydro-1,6,7,8-indolizinetetrol 6-(4-fluorobenzoate) | 0.500 g |
| polyoxyethylene sorbitan monooleate | 2.000 g |
| sodium chloride | 0.128 g |
| water for injection qs ad | 20.000 ml |

What is claimed is:

1. A method of treating a Herpes viral infection in a patient in need thereof which comprises administering to the patient an anti-Herpes virally effective amount of a castanospermine ester of the formula:

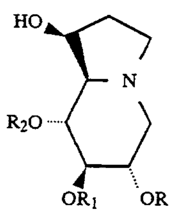

wherein R, $R_1$ and $R_2$ are each independently hydrogen, $C_{1-14}$ alkanoyl, $C_{1-14}$ alkenoyl, cyclohexanecarbonyl, $C_{1-8}$ alkoxyacetyl,

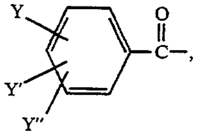

naphthalenecarbonyl optionally substituted by methyl or halogen; phenyl ($C_{2-6}$ alkanoyl) wherein the phenyl is optionally substituted by methyl or halogen; cinnamoyl; pyridinecarbonyl optionally substituted by methyl or halogen; dihydropyridine carbonyl optionally substituted by $C_1$-$C_{10}$ alkyl; thiophenecarbonyl optionally substituted by methyl or halogen; or furancarbonyl optionally substituted by methyl or halogen; Y is hydrogen, $C_{1-4}$ alkyl, $C_{1-4}$ alkoxy, halogen, trifluoromethyl, $C_{1-4}$ alkylsulfonyl, $C_{1-4}$ alkylmercapto, cyano or dimethylamino; Y' is hydrogen, $C_{1-4}$ alkyl, $C_{1-4}$ alkoxy, halogen or it is combined with Y to give 3,4-methylenedioxy; Y'' is hydrogen, $C_{1-4}$ alkyl, $C_{1-4}$ alkoxy or halogen; with R, $R_1$ and $R_2$ being selected in such a way that at least one of them, but not more than two of them, is hydrogen; or a pharmaceutically acceptable salt thereof.

2. A method of treating a Herpes viral infection with a castanospermine ester of claim 1 wherein R, $R_1$ and $R_2$ are each independently hydrogen, $C_{1-10}$ alkanoyl, $C_{1-10}$ alkanoyl, $C_{1-8}$ alkoxyacetyl, or wherein Y is hydrogen, $C_{1-4}$ alkyl, $C_{1-4}$ alkoxy,

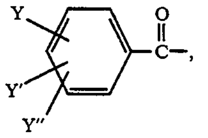

halogen, trifluoromethyl, $C_{1-4}$ alkylsulfonyl, $C_{1-4}$ alkylmercapto, cyano or dimethylamino; Y' is hydrogen, $C_{1-4}$ alkyl, $C_{1-4}$ alkoxy, halogen or it is combined with Y to give 3,4-methylenedioxy; Y" is hydrogen, $C_{1-4}$ alkoxy or halogen; with R, $R_1$ and $R_2$ being selected in such a way that at least one of them, but not more than two of them, is hydrogen; or a pharmaceutically acceptable salt thereof.

3. A method of treating a Herpes viral infection with a castanospermine ester of claim 1 wherein R, $R_1$ and $R_2$ are each independently hydrogen, $C_{1-8}$ alkanoyl, $C_{1-8}$ alkanoyl, $C_{1-8}$ alkoxy-acetyl, or a benzoyl optionally substituted with an alkyl or halogen; with R, $R_1$ and $R_2$ being selected in such a way that at least one of them, but not more than two of them, is hydrogen; or a pharmaceutically acceptable salt thereof.

4. A method of treating a Herpes viral infection with a castanospermine ester of claim 1 wherein R, $R_1$ and $R_2$ are each independently hydrogen, $C_{1-8}$ alkanoyl, $C_{1-8}$ alkanoyl, $C_{1-8}$ alkoxy-acetyl or a benzoyl optionally substituted with a methyl, bromo, chloro, or fluoro group; with R, $R_1$ and $R_2$ being selected in such a way that at least one of them, but not more than two of them, is hydrogen; or a pharmaceutically acceptable salt thereof.

5. A method of treating a Herpes viral infection with a castanospermine ester of claim 1 wherein $R_1$ is a $C_{1-8}$ alkanoyl, $C_{1-10}$ alkanoyl, $C_{1-8}$ alkoxyacetyl, or benzoyl optionally substituted with an alkyl or halogen group; or a pharmaceutically acceptable salt thereof.

6. A method of treating a Herpes viral infection with a castanospermine ester of claim 1 wherein $R_1$ is a $C_{1-8}$ alkanoyl, $C_{1-8}$ alkanoyl, $C_{1-8}$ alkoxyacetyl, or benzoyl optionally substituted with a methyl, bromo, chloro, or fluoro group or a pharmaceutically acceptable salt thereof.

7. A method of treating a Herpes viral infection with a castanospermine ester of claim 1 which is -octahydro-1,6,7,8-indolizinetetrol 6-benzoate.

8. A method of treating a Herpes viral infection with a castanospermine ester of claim 1 which is -octahydro-1,6,7,8-indolizinetetrol 7benzoate.

9. A method of treating a Herpes viral infection with a castanospermine ester of claim 1 which is -octahydro-1,6,7,8-indolizinetetrol 6-(4-methylbenzoate).

10. A method of treating a Herpes viral infection with a castanospermine ester of claim 1 which is -octahydro-1,6,7,8-indolizinetetrol 7-(4bromobenzoate).

11. A method of treating a Herpes viral infection with a castanospermine ester of claim 1 which is -octahydro-1,6,7,8-indolizinetetrol 6,8-dibutanoate.

12. A method of treating a Herpes vital infection with a castanospermine ester of claim 1 which is -octahydro-1,6,7,8-indolizinetetrol 6-butanoate.

13. A method of treating a Herpes viral infection with a castanospermine ester of claim 1 which is -octahydro-1,6,7,8-indolizinetetrol 6-(2-furancarbonxylate).

14. A method of treating a Herpes viral infection with a castanospermine ester of claim 1 which is -octahydro-1,6,7,8-indolizinetetrol 7-(2,4-dichlorobenzoate).

15. A method of treating a Herpes viral infection with a castanospermine ester of claim 1 which is -octahydro-1,6,7,8-indolizinetetrol 6-(3-hexenoate).

16. A method of treating a Herpes vital infection with a castanospermine ester of claim 1 which is -octahydro-1,6,7,8-indolizinetetrol 6-octanoate.

17. A method of treating a Herpes viral infection with a castanospermine ester of claim 1 which is -octahydro-1,6,7,8-indolizinetetrol 6-pentanoate.

* * * * *

UNITED STATES PATENT AND TRADEMARK OFFICE

CERTIFICATE OF CORRECTION

PATENT NO. : 5,385,911

DATED : January 31, 1995

INVENTOR(S) : Sai P. Sunkara, Paul S. Liu, A. Stanley Tyms, Debra L. Taylor

It is certified that error appears in the above-indentified patent and that said Letters Patent is hereby corrected as shown below:

Column 1, line 53 the patent reads "abdoman" and should read --abdomen--.

Column 2, line 6 the patent reads "negligable" and should read --negligible--.

Column 2, line 16 the patent reads "vital membrane" and should read --viral membrane--.

Column 2, line 32 the patent reads "vital replication" and should read --viral replication--.

Column 6, line 24 the patent reads "obtained form" and should read --obtained from--.

Column 6, line 37 the patent reads "who as" and should read --who has--.

Column 6, line 38 the patent reads "been in infected and should read --been infected--.

Column 7, line 23 the patent reads "by either by and should read --by either--.

Column 8, line 21 the patent reads "pharmaceutically acceptably" and should read --pharmaceutically acceptable--.

Column 8, line 38 the patent reads "carhomers" and should read --carbomers--.

Column 8, line 39 the patent reads "carboxymethylcelluiose" and should read --carboxymethylcellulose--.

Column 9, line 49 the patent reads "*in vauco*" and should read "*in vacuo*".

UNITED STATES PATENT AND TRADEMARK OFFICE

CERTIFICATE OF CORRECTION

PATENT NO. : 5,385,911

DATED : January 31, 1995

INVENTOR(S) : Sai P. Sunkara, Paul S. Liu, A. Stanley Tyms, Debra L. Taylor

It is certified that error appears in the above-indentified patent and that said Letters Patent is hereby corrected as shown below:

Column 9, line 65 the patent reads "(m, 1H, $C_1$-M)," and should read --(m, 1H, $C_1$-H)--.

Column 10, line 34 that patent reads "(m, 1H, $C_1$-M)," and should read --(m, 1H, $C_1$-H)--.

Column 11, line 14 the patent reads "liltrate" and should

Column 11, line 16 the patent reads "8-indolizine-tetrol" and should read --8-indolizinetetrol--.

Column 12, line 5 the patent reads "(160, 6β," and should read --(1α, 6β,--.

Column 12, line 56 the patent reads "form" and should read --from--.

Column 12, line 66 the patent reads "chloride, the combine" and should read --chloride, the combined--.

Column 13, line 19 the patent reads "*in vacuo* give" and should read --*in vacuo* to give--.

Column 13, line 20 the patent reads "recrystallised" and should read --recrystallized--.

Column 13, line 25 the patent reads "form" and should read --from--.

Column 16, line 10 the patent reads "7benzoate" and should read --7-benzoate--.

Column 16, line 17 the patent reads "(4bromobenzoate)" and should read --(4-bromobenzoate)--.

Column 16, line 21 the patent reads "vital" and should read --viral--.

UNITED STATES PATENT AND TRADEMARK OFFICE

CERTIFICATE OF CORRECTION

PATENT NO. : 5,385,911

DATED : January 31, 1995

INVENTOR(S) : Sai P. Sunkara, Paul S. Liu, A. Stanley Tyms, Debra L. Taylor

It is certified that error appears in the above-indentified patent and that said Letters Patent is hereby corrected as shown below:

Column 16, line 26 the patent reads "furancarbonxylate" and should read --furancarboxylate--.

Signed and Sealed this

Twenty-ninth Day of October 1996

Attest:

BRUCE LEHMAN

*Attesting Officer* — *Commissioner of Patents and Trademarks*